US005947288A

United States Patent [19]
Dykstra et al.

[11] Patent Number: 5,947,288
[45] Date of Patent: Sep. 7, 1999

[54] PEEL POUCH

[75] Inventors: Scott M. Dykstra, Jenison; Mark S. Lastovich, Rockford, both of Mich.

[73] Assignee: Oliver Products Company, Grand Rapids, Mich.

[21] Appl. No.: 09/179,811

[22] Filed: Oct. 27, 1998

[51] Int. Cl.[6] .................................................. B65D 27/32
[52] U.S. Cl. ....................... 206/439; 206/484.2; 383/111
[58] Field of Search .................... 383/109, 111, 383/113; 206/438, 439, 484, 484.1, 484.2

[56] References Cited

U.S. PATENT DOCUMENTS

| | | | |
|---|---|---|---|
| 3,403,776 | 10/1968 | Denny | 206/56 |
| 3,754,700 | 8/1973 | Bonk | 229/62 |
| 4,352,429 | 10/1982 | Newman | 206/439 |
| 4,660,721 | 4/1987 | Mykleby | 206/439 |
| 4,671,393 | 6/1987 | Rainey | 383/111 X |
| 5,222,600 | 6/1993 | Stoddard | 206/370 |
| 5,341,922 | 8/1994 | Cerwin et al. | 206/484.2 X |
| 5,459,978 | 10/1995 | Weiss | 53/425 |
| 5,551,781 | 9/1996 | Wilkes et al. | 206/439 X |
| 5,590,777 | 1/1997 | Weiss | 206/439 |
| 5,653,090 | 8/1997 | Weiss | 53/425 |

*Primary Examiner*—Jacob K. Ackun
*Attorney, Agent, or Firm*—Price, Heneveld, Cooper, DeWitt & Litton

[57] ABSTRACT

A sterilizable pouch package for medical objects or the like, comprising, a first layer of material, a second layer of film on said first layer, a third layer of film on said second layer, the layers being sealed together in a peripheral seal to form a space between the second and third layers for an object, the seal between the first layer and the second and third layers being releasable by tensile separation of the first layer from the second and third layers, and the second layer having a breakable perforation line at the space whereby the second layer can be broken at the perforation line to expose a portion of the object for direct presentation of the object from one person to another person.

18 Claims, 3 Drawing Sheets

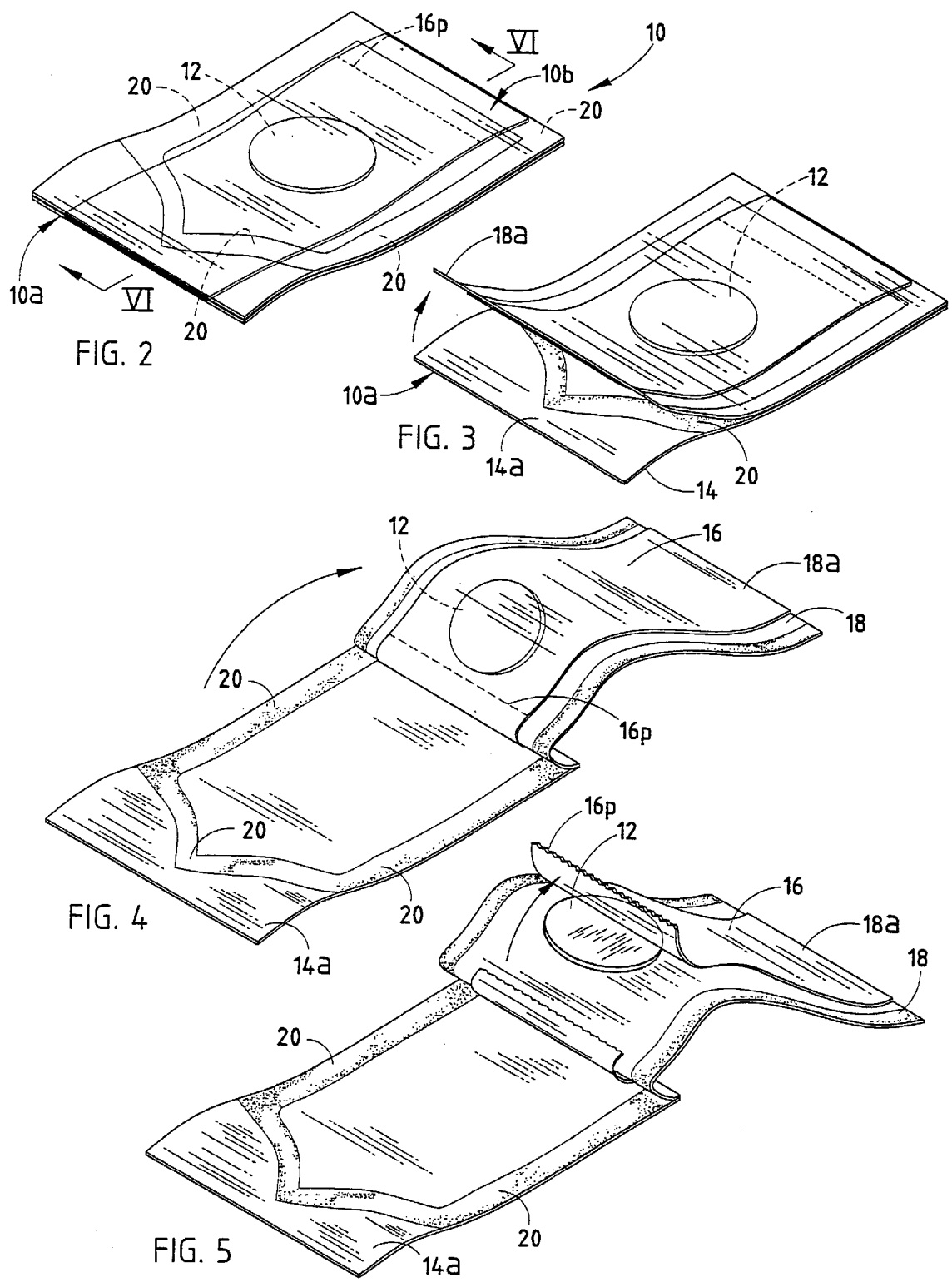

PEEL POUCH

BACKGROUND OF THE INVENTION

This invention relates to a sterilizable pouch and a method of making the same. Sterile objects for medical use are retained in packaging intended to allow the sterile object to be uncontaminated when presented to a doctor or surgeon for his/her use. There are presently two primary techniques for retaining sterility. In the first technique, a portion of the peripheral seal of the sterile package (see FIG. 8) is broken between the two layers of the package, and the sterile object is then slid out of the package without touching it, onto a sterile surface such as a table (see FIG. 9), from which the doctor/surgeon removes the object for use in the medical procedure or surgery. Having to use this intermediate sterile surface is a significant disadvantage. A second technique which takes special training to achieve by the medical assistant is accomplished by pulling the sterile package layers apart at one end, peeling or folding back the two layers in opposite directions (see FIG. 10) while the assistant is grasping a portion of the object through the two layers, and allowing the doctor/surgeon to take the object directly from the package as it is presented to him by the nurse or assistant. This technique can result in dropping of the object or other inadvertent contamination of the sterile object.

SUMMARY OF THE INVENTION

The present invention enables an object such as a sterile medical object to be sterilized in the packaging, the package retaining the sterility of the object, but later enabling easy presentation and removal of the object from the package without having to use either of the prior techniques mentioned above. Rather, the object can be presented directly to the surgeon without contact by the presenter, e.g., a nurse, and with minimal possibility of mishap to cause inadvertent contamination of the sterile object.

The package constitutes a unique three layer assembly with the layers being any of several different materials such as polymer, paper, or composite materials such as a paper-polymer combination. The base or first layer may thus be of a selected material and preferably is of a nonwoven, breathable, spun polymeric material, as of a polyolefin, e.g., a material marketed as Tyvek®, by E.I. Du Pont Company. The second, i.e., middle layer, is of selected material and preferably constitutes a polymer film, most preferably transparent, as of polyethylene. The third, i.e., top layer, is of selected material, preferably a polymer film, most preferably transparent, such as a polyester polyethylene copolymer. The sterile object is retained between layers two and three. The second, middle layer, has a transverse perforation line thereacross, which allows it to be broken open at the appropriate time. The sterile object can be removed in a protected fashion by breaking the seal between layer one and the joined layers two and three by pulling the sections apart using protruding gripping flanges, finger force then being applied to break the perforation line so layer one, a portion of broken layer two, and the overlapping portion of layer three can be folded back to expose a portion of the sterile object to enable the surgeon's assistant to present the exposed portion of the sterile object directly to the surgeon for his/her grasp.

These and other features, advantages and objects of the present invention will be further understood and appreciated by those skilled in the art by reference to the following specification, claims and appended drawings.

BRIEF DESCRIPTION OF THE DRAWINGS

FIG. 2 is a perspective view of the sterilized object in its packaging;

FIG. 3 is a perspective view depicting the first step in opening the sterile package by grasping flanges and peeling layers two and three away from base layer one;

FIG. 4 is a perspective view showing the further opening of package layers two and three from base layer one;

FIG. 5 is a perspective view depicting the breakage of the perforation line by finger pressure on the underside of the object against the film layer two having the perforation line, for direct access and grasping of the sterile object by a doctor/surgeon;

DETAILED DESCRIPTION OF PREFERRED EMBODIMENT

Figure 1:
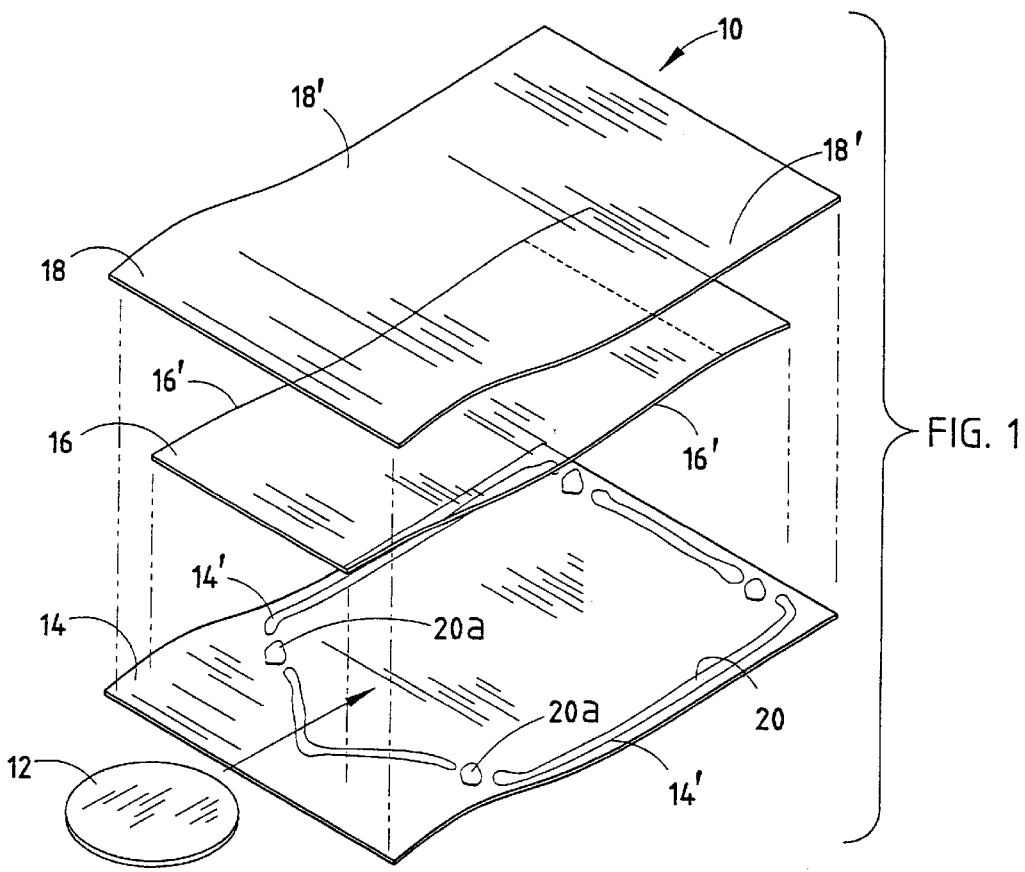
FIG. 1 is an exploded view of the three layers of the package pouch and a representative sterile object shown simply as a disc for illustrative purposes.
Figure 6:
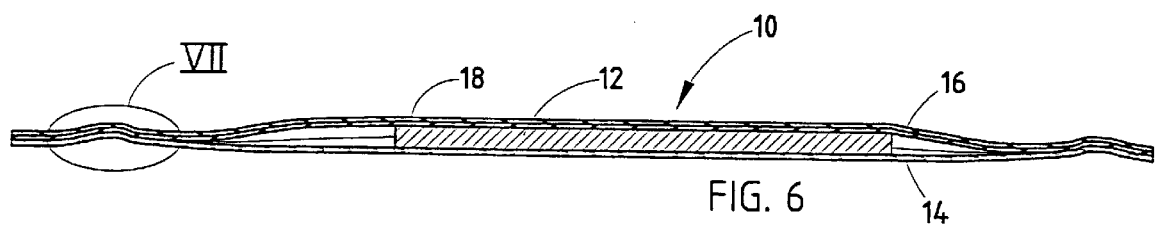
FIG. 6 is a sectional elevational view of the package and sterile item taken on plane VI—VI of FIG. 2.
Figure 7:
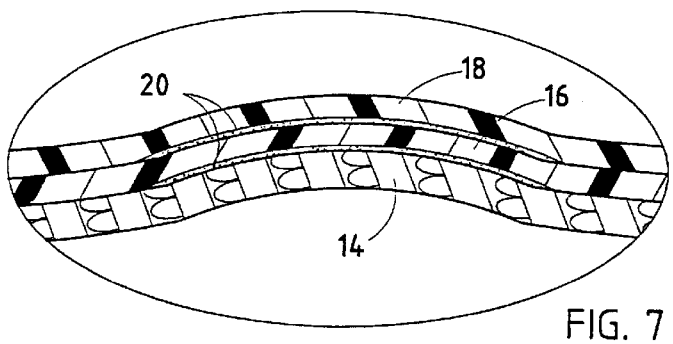
FIG. 7 is an enlarged sectional view of the three layers of the pouch at the corner junctions in the area VII of FIG. 6.
Figure 8:
FIG. 8 is a side elevational sectional view of a prior art packaged sterile object.
Figure 9:
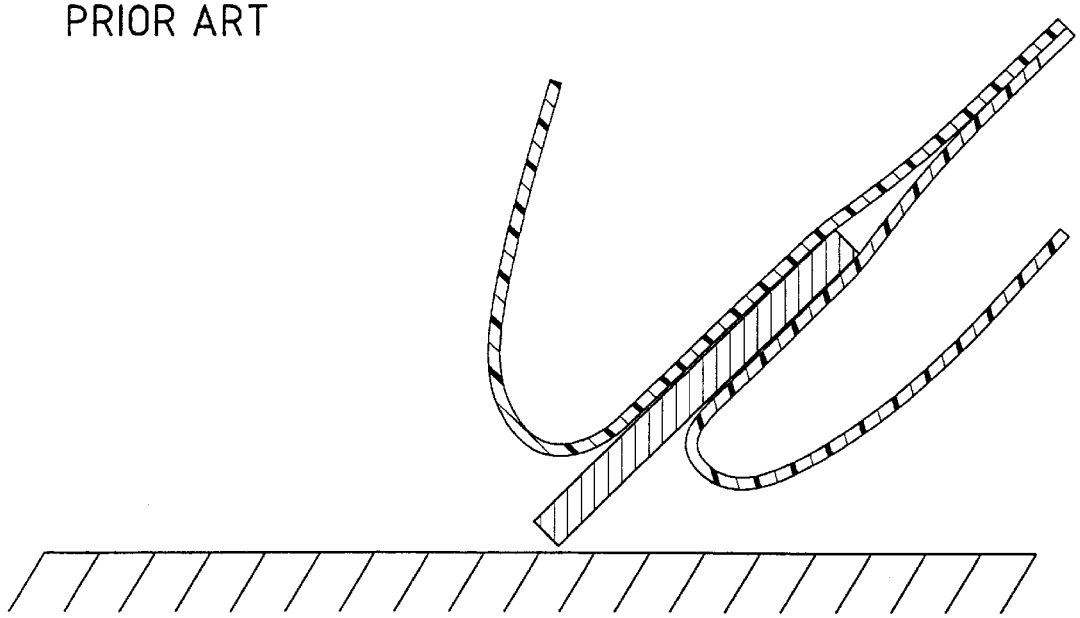
FIG. 9 is a side elevational sectional view of the object in FIG. 8 being placed on a sterile surface in accordance with one prior art technique.
Figure 10:
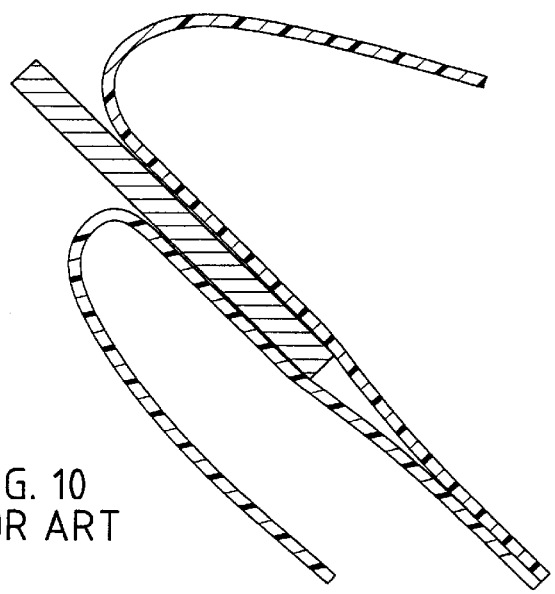
FIG. 10 is a sectional elevational view of the prior art object and package in FIG. 8 shown with the package layers peeled back for presentation of the item to a surgeon in accordance with another prior art technique.

For purposes of clarity, the invention is described in its orientation depicted, it being realized that descriptors such as "up," "down," "top," "bottom," "base," and the like are not limitations, but just used as explanatory terms. Referring now specifically to the drawings, the pouch package assembly 10 is shown to include a representative sterilized object 12 within the sealed assembly. The pouch comprises three layers, namely a base layer 14 preferably of a breathable, nonwoven, spun bonded, polyolefin material such as Tyvek® brand; the second layer, i.e., middle layer 16, such as a flexible heat sealable polymer, preferably translucent, and most preferably transparent, as of polyethylene, and the third layer, shown as a top layer 18, comprising a heat sealable polymeric layer, preferably transparent, as of polyester polyethylene copolymer. Middle layer 16 is of like length to layers 14 and 18, but narrower from side to side so as to not be sealed along the side edges 16' when the side edges 18' of third layer 18 are sealed to the first layer side edges 14' as will be described. Middle layer 16 has a transverse perforation line 16p that extends thereacross between its side edges, and within the space defined by the side seals. The layers are joined together, preferably by a heat seal, optionally utilizing a hot melt adhesive 20 such as EVA which is applied along the two side edges 14' of lower layer 14, and along one end of layer 14 spaced from the end edge (left end in FIG. 2). The spacing of the seals, i.e., of adhesive 20, from the end edge of layer 14 allows layer 14 to have an extending gripping flange 14a (FIG. 3) i.e. extending beyond the adjacent end seal, and the combined second and third layers to have an extending gripping flange 18a extending beyond the adjacent end seal, for gripping and pulling them apart by the fingers of both hands as generally depicted by the arrow in FIG. 3. Use of a heat sealing adhesive 20 assures excellent sealing between a porous layer 14 and imperforate films 16 and 18. At the side edges of the pouch, the edges of layer 18 are sealed directly to the edges of layer 14. The side edges of the middle layer 16 are preferably unsealed. After the object 12 is in place in the pouch through the unsealed end, all three layers at the remaining unsealed end edge 10b (the right end in FIG. 2) are sealed together, while as noted previously, at the other end 10a of the pouch all three layers have already been sealed together spaced from those end edges. At the juncture of the side edges of middle layer 16 with the seal, as depicted at locations 20a in FIG. 1, the seal should assure sufficient adhesive to serve as caulking of the side edges of middle layer 16 for a barrier to contamination.

The pouch can be manufactured and delivered by one company to another company or party for insertion and sterilization of the object and pouch. Manufacture of the pouch includes the step of overlaying the three layers and effecting the seal along the two side edges and just one end 10a (FIG. 2) of the pouch, but leaving end 10b unsealed. The object 12 is inserted between the second and third layers 16 and 18 through this unsealed end 10b. End 10b is then sealed to bond all three layers together. The product and pouch are then sterilized in a conventional manner such as by steam, ETO (ethylene oxide) or gamma radiation.

When the sterile object 12 is to be employed in a medical procedure or surgery, the assistant or nurse grasps flange 14a of layer 14 and joined double flange 18a of layers 16 and 18 at end 10a of the pouch, and peels them apart as shown in FIGS. 3 and 4. At this time, object 12 is still between layers 16 and 18. Then, by applying finger pressure to one side of the object (the underside as depicted in FIGS. 4 and 5) and thumb pressure to the other side of the object, layer 16 is broken across perforation line 16p that extends transversely across the entire width of layer 16 near end 10b of the pouch, i.e., generally on the opposite end of the inner pouch space from flanges 14a and 18a. Breakage of this perforation line 16p while grasping with the thumb and fingers the opposite sides of one portion of object 12 enables this portion of the object to be held by the assistant while another portion of the object is exposed and presented directly to the surgeon for his grasp of this exposed portion.

Experimental usage of the novel pouch has shown it to function very effectively.

The above description is considered that of the preferred embodiment only. Modifications of the invention will occur to those skilled in the art and to those who make or use the invention. For example, the generally rectangular configuration of the depicted pouch can be any of a variety of shapes. Also, the chevron shape of the seal can be a different configuration. Therefore, it is understood that the embodiment shown in the drawings and described above is merely for illustrative purposes and not intended to limit the scope of the invention, which is defined by the following claims as interpreted according to the principles of patent law, including the doctrine of equivalents.

What is claimed is:

1. A sterilizable pouch package for medical objects or the like, comprising:

a first layer of material;

a second layer on said first layer;

a third layer on said second layer;

said layers being sealed together in a peripheral seal to form a space between said second and third layers for an object;

said seal between said first layer and said second and third layers being releasable by tensile separation of said first layer from said second and third layers;

said second layer having a breakable perforation line at said space whereby said second layer can be broken at said perforation line to expose a portion of the object in said space for direct presentation of the object from one person to another person.

2. The sterilizable pouch package in claim 1 wherein said peripheral seal is incomplete along one peripheral portion of said pouch to allow insertion of an object in said space, followed by completing said peripheral seal at said peripheral portion.

3. The sterilizable pouch package in claim 1 wherein said first layer and said second and third layers have graspable flanges extending outwardly beyond said seal, to enable separation of said first layer from said second and third layers, followed by breakage of said perforation line.

4. The sterilizable pouch package in claim 3 wherein said perforation line is located generally on the opposite end of said space from said flanges.

5. The sterilizable pouch package in claim 1 wherein said seal is a heat seal.

6. The sterilizable pouch package in claim 5 wherein said seal employs a heat seal adhesive.

7. The sterilizable pouch package in claim 1 wherein said first, second and third layers have opposite side edges, and said second layer side edges terminate short of said first and third layer side edges and short of said seal at said side edges.

8. The sterilizable pouch package in claim 1 wherein said first layer is of nonwoven, spun, bonded, olefin material.

9. The sterilizable pouch package in claim 8 wherein said second and third layers are of polymeric material.

10. The sterilizable pouch package in claim 9 wherein said third layer is translucent.

11. A sterilizable pouch package for medical objects or the like, comprising:

a first layer of material;

a second layer on said first layer;

a third layer on said second layer;

said layers being sealed together in a peripheral seal to form a space between said second and third layers for an object;

said seal between said first layer and said second and third layers being releasable by tensile separation of said first layer from said second and third layers;

said second layer having a breakable perforation line at said space whereby said second layer can be broken at said perforation line to expose a portion of the object in said space for direct presentation of the object from one person to another person.

12. The sterilizable pouch package in claim 11 wherein said peripheral seal is incomplete along one peripheral portion of said pouch to allow insertion of an object in said space, followed by completing said peripheral seal at said peripheral portion.

13. The sterilizable pouch package in claim 11 wherein said first layer and said second and third layers have graspable flanges extending outwardly beyond said seal, to enable separation of said first layer from said second and third layers, followed by breakage of said perforation line.

14. The sterilizable pouch package in claim 13 wherein said perforation line is located generally on the opposite end of said space from said flanges.

15. The sterilizable pouch package in claim 11 wherein said seal is a heat seal.

16. The sterilizable pouch package in claim 15 wherein said seal employs a heat seal adhesive.

17. The sterilizable pouch package in claim 11 wherein said first, second and third layers have opposite side edges, and said second layer side edges terminate short of said first and third layer side edges and short of said seal at said side edges.

18. The sterilizable pouch package in claim 11 wherein said first layer is of nonwoven, spun, bonded, olefin material.

* * * * *